(12) United States Patent
Kabakov

(10) Patent No.: US 8,491,481 B2
(45) Date of Patent: Jul. 23, 2013

(54) SYSTEM AND METHOD FOR MEASURING THE INSTANTANEOUS PERIOD OF A QUASI-PERIODIC SIGNAL

(75) Inventor: Serguei Kabakov, Laurel, MD (US)

(73) Assignee: General Electric Company, Schenectady, NY (US)

( * ) Notice: Subject to any disclaimer, the term of this patent is extended or adjusted under 35 U.S.C. 154(b) by 1004 days.

(21) Appl. No.: 12/361,924

(22) Filed: Jan. 29, 2009

(65) Prior Publication Data

US 2010/0191118 A1   Jul. 29, 2010

(51) Int. Cl.
*A61B 8/00* (2006.01)

(52) U.S. Cl.
USPC ............ 600/453; 600/516; 600/517; 600/521

(58) Field of Classification Search
USPC .......... 600/453, 509, 521, 516–519, 523–524
See application file for complete search history.

(56) References Cited

U.S. PATENT DOCUMENTS

| | | | |
|---|---|---|---|
| 3,982,528 A | 9/1976 | Phillipps | |
| 3,991,365 A | 11/1976 | Takeuchi | |
| 4,569,356 A | 2/1986 | Kyozuka | |
| 4,573,479 A | 3/1986 | Tuccillo | |
| 4,924,875 A * | 5/1990 | Chamoun | 600/509 |
| 5,123,420 A | 6/1992 | Paret | |
| 5,170,791 A | 12/1992 | Boos et al. | |
| 5,255,186 A * | 10/1993 | Steinhaus et al. | 600/519 |
| 5,584,295 A * | 12/1996 | Muller et al. | 600/300 |
| 5,924,980 A | 7/1999 | Coetzee | |
| 2002/0183637 A1 | 12/2002 | Kim et al. | |
| 2008/0194978 A1 * | 8/2008 | Beker et al. | 600/516 |
| 2010/0074475 A1 | 3/2010 | Chouno | |

FOREIGN PATENT DOCUMENTS

WO   2008044572 A1   4/2008

OTHER PUBLICATIONS

Boos, Andreas et al; A New, Lightweight Fetal Telemetry System; Hewlett-Packard Juornal; Dec. 1995; pp. 82-93.
Je_Ewski, Janusz; Monitoring of mechanical and electrical activity of fetal heart: Determination of the FHR; Archives of Perinatal Medicine 8(1), 2002; pp. 33-39. [Abstract].
Lee, J.H. et al; Fast cross-correlation method for real time detection of fetaiheart rate; Engineering in Medicine and Biology Society, 1998, Proceedings of the 20th Annual International Conference of the IEEE; vol. 1, Issued Oct. 29-Nov. 1, 1998; pp. 178-181. [Abstract].
Pretlow, Robert A. III et al; Signal Processing Methodologies for an Acoustic Fetal Heart Rate Monitor; Sep. 1992; Department of Electrical & Computer Engineering College of Engineering & Technology, Old Dominion University; Norfolk, VA 23529; (see pp. 23-25).

(Continued)

*Primary Examiner* — Tse Chen
*Assistant Examiner* — Joel F Brutus
(74) *Attorney, Agent, or Firm* — Andrus, Sceales, Starke & Sawall, LLP

(57) ABSTRACT

A method of measuring the instantaneous period of a quasi-periodic signal includes determining an initial template, performing a cross-correlation between the initial template and a quasi-periodic signal and selecting portions of the signal that correspond to the peaks of the correlation signal. The selected portions are then averaged and another cross correlation is performed between the quasi-periodic signal and a template including the averaged selected portions. The instantaneous period is then measured from the correlation signal.

10 Claims, 14 Drawing Sheets

OTHER PUBLICATIONS

Schlindwein, Fernando S. et al; Noninvasive Determination of Fetal Heart Rate and Short Term Heart Rate Variability Using Solely Doppler Ultrasound With Autocorrelation.

Smith, J.H. et al; Improvements in the registration and analysis of fetal heart rate records at the bedside; Obstet Gynaecol.; Apr. 1985; 92 (4); pp. 317-325. [Abstract].

Spencer, J.A.; Current methods of continuous fetal heart rate monitoring; Prof. Nurse, Dec. 1992; 8(3); pp. 173-175. [Abstract].

Tuck, D.L. et al; Improvement in Doppler ultrasound human foetal heart rate records by signal correlation; Medical & Biological Engineering & Computing, May 1982; vol. 20; pp. 357-360. [Abstract].

Hua, Xiao et al; A new algorithm for detecting fetal heart rate using ultrasound Doppler signals; Ultrasonics, vol. 43, Issue 6, May 2005, pp. 399-403. [Abstract].

Xiong, Xianming et al; DSP-based Design of Ultrasound Doppler Fetal Heart Rate Monitor; Guilin University of Electronic Technology. [Abstract].

Yamakoshi, Yoshiki et al; Fetal Heart Rate Estimation by an Ultrasonic Wave Direct Digital Detection and Complex Auto Correlation; Transactions of the Institute of Electronics; 2001; vol. J84; No. 12, pp. 1414-1420. [Abstract].

Zhang, C. et al; An improved auto-correlation method for Doppler fetal heart rate measurement. [Abstract].

Zhi-Lin, Zhang et al; A Two-Stage Based Approach for Extracting Periodic Signals; ICA 2006; LNCS 3889; 2006; pp. 303-310.

Extended Search Report and Written Opinion from corresponding EP Application No. 10151146.7, Nov. 7, 2011.

\* cited by examiner

US Signal (X)

Correlation of (x) with T₂

SYSTEM AND METHOD FOR MEASURING THE INSTANTANEOUS PERIOD OF A QUASI-PERIODIC SIGNAL

BACKGROUND

The current disclosure relates to the field of digital signal processing. More specifically, the present disclosure relates to a system and method of measuring the instantaneous period of a quasi-periodic signal.

Many monitored signals may be characterized as quasi-periodic signals. These signals exhibit a generally repeating wave form, but at a constantly changing frequency. One such example of a quasi-periodic signal is a returned ultrasound signal exhibiting a Doppler effect. The Doppler effect may be due to the motion of a fetus' beating heart. While ultrasound signals have a variety of applications in medical and other fields, including imaging, diagnostic, and therapeutic applications, one such application is the use of ultrasound signals to monitor fetal heart rate.

In the measurement of fetal heart rate (FHR), it is desirable to be able to determine the instantaneous period of the fetal heart activity at each heart beat. The determination of beat to beat fetal heart rate can have additional diagnostic value in determining the condition of the fetus compared to an average fetal heart rate alone.

One of the problems facing the accurate measurement of instantaneous fetal heart rate is that measurements of instantaneous period are highly susceptible to noise and other artifacts in the ultrasound signal. This issue is commonly addressed by taking the average period over a plurality of intervals in order to filter out some of the noise. This reduces the noise, but decreases the accuracy of the instantaneous heart rate determination as the heart rate measurement is based upon multiple beats. More accurate results may be obtained by shortening the length of the measurement window, but as the number of heart beats used for the determination is reduced, the susceptibility to noise and artifacts increases. Therefore, a balance must be struck when selecting the number of beats over which the signal is averaged to balance the noise reduction and heart rate determination accuracy considerations.

BRIEF DISCLOSURE

In one disclosed method of measuring the instantaneous period of a quasi-periodic signal, the method includes obtaining a quasi-periodic signal, determining an initial template of a determined size and shift, and performing a cross-correlation between the initial template and the quasi-periodic signal to obtain an initial correlation signal. Next a first correlation threshold is established and portions of the quasi-periodic signal are selected that correspond to the peaks of the initial correlation signal that are greater than the first correlation threshold. The selected portions are then averaged to create a second template. A cross correlation is performed between the second template and the quasi-periodic signal to obtain a second correlation signal. Then the instantaneous period is measured.

In an alternative embodiment, a method of measuring a fetal heart rate from an ultrasound signal is disclosed. This method includes the steps of obtaining an ultrasound signal that includes a first segment and a second segment, processing the first segment of the ultrasound signal by selecting a portion of the first segment as a template, performing a correlation between a first template and the first segment to obtain an initial correlation signal with a first peak and a second peak, and measuring the fetal heart rate of the first segment between the first peak and the second peak. The measured instantaneous period of the first segment is then reported. The second segment is then processed by establishing a first correlation threshold, performing a cross-correlation between a first template and the second segment to obtain a first correlation signal, and measuring the fetal heart rate across the second segment.

A system for measuring an instantaneous fetal heart rate using an ultrasound transducer is also disclosed. The system includes an ultrasound transducer attached to the abdomen of a patient. A correlation computer applies a current template to an ultrasound signal segment to calculate a cross-correlation between the current template and the ultrasound signal segment to produce a current correlation signal. A peak detector identifies a plurality of peaks of the current correlation signal that exceeds a threshold. A template creator is connected to the peak detector and the correlation computer and averages the portions of the ultrasound signal segment that correspond to the detected peaks in the current correlation signal to create a new template. A fetal heart rate detector measures the instantaneous period of the current correlation signal to determine a measurement of fetal heart rate, and a graphical display presents the measurement of fetal heart.

DETAILED DISCLOSURE

Many monitored signals are quasi-periodic signals. Often, it is desirable to accurately measure the instantaneous period of the signals. One such example of a quasi-periodic signal is the heart rate of an unborn fetus. This heart rate may be obtained by an ultrasound transducer that produces a constantly changing graph of the Doppler shift of the sound waves produced by the transducer as they are received after reflecting off of the fetus and passing through the mother's abdomen. While the present disclosure will focus on the example of monitoring fetal heart rate, it is to be understood that the present disclosure may be similarly applicable to a wide variety of other monitored quasi-periodic signals.

Figure 1:
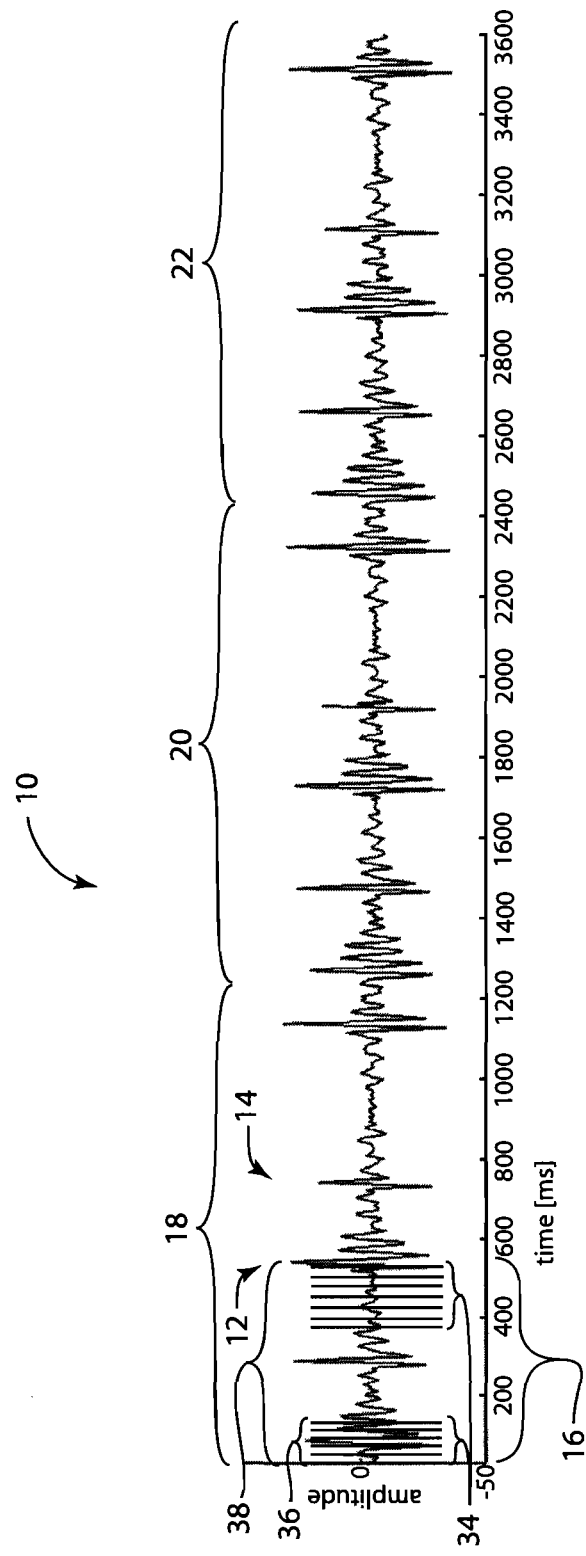
FIG. 1 is a diagram of an ultrasound signal.

FIG. 1 depicts an exemplary graph of an ultrasound signal 10 obtained when monitoring fetal heart rate. The ultrasound signal 10 includes a plurality of generally repeating wave-forms. Each heart beat of the fetus registers in the ultrasound signal 10 as a complimentary pair of pulses corresponding to the two basic functional movements of the heart. The first wave form 12 corresponds to the contraction of the ventricles and the second wave form 14 corresponds to the closure of the semilunar valves. The ultrasound signal 10 of FIG. 1 is a quasi-periodic signal in that while the signal is generally repeating, the frequency of the signal is constantly shifting over a frequency range. The fetal heart frequently beats within a typical range of 30-300 beats per minute.

Figure 2A:
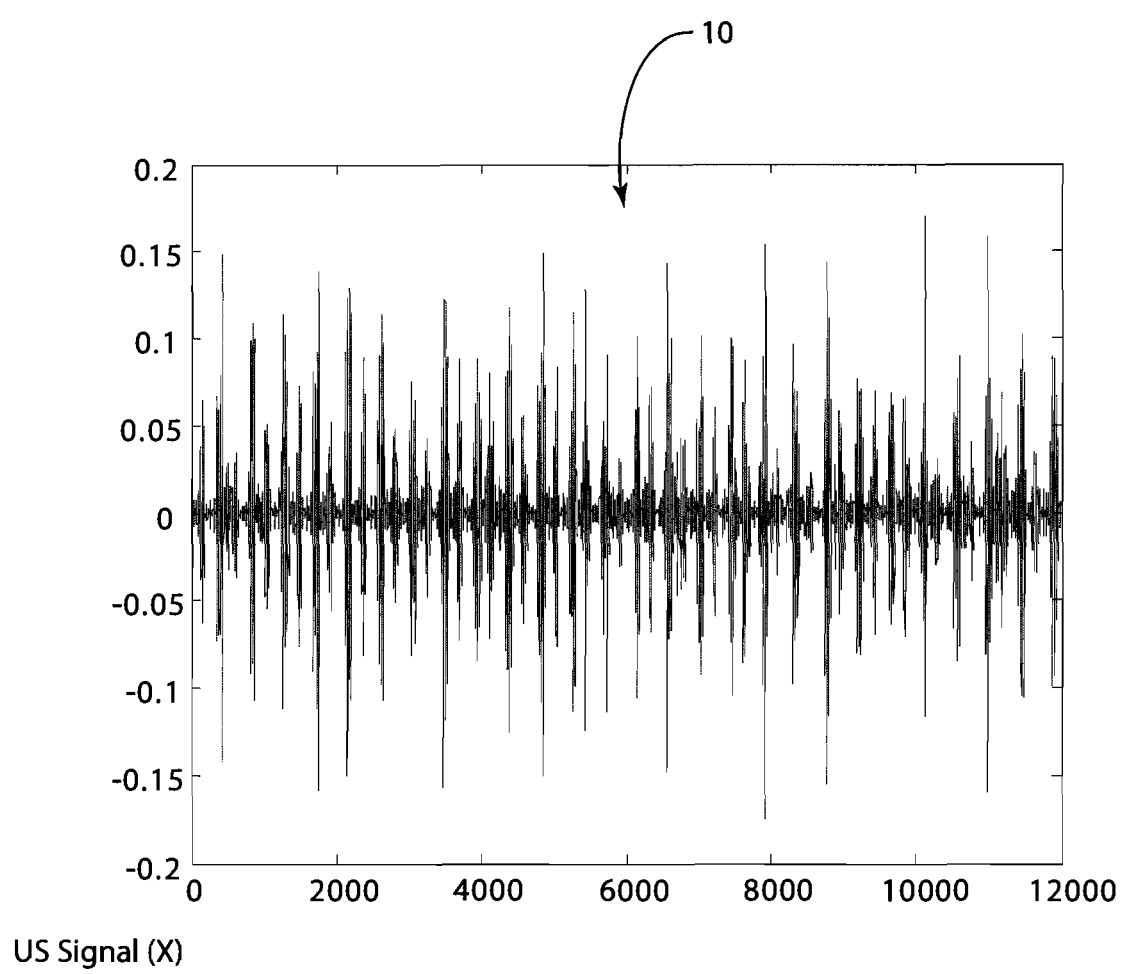
FIGS. 2A-D depict exemplary signals.
Figure 2B:
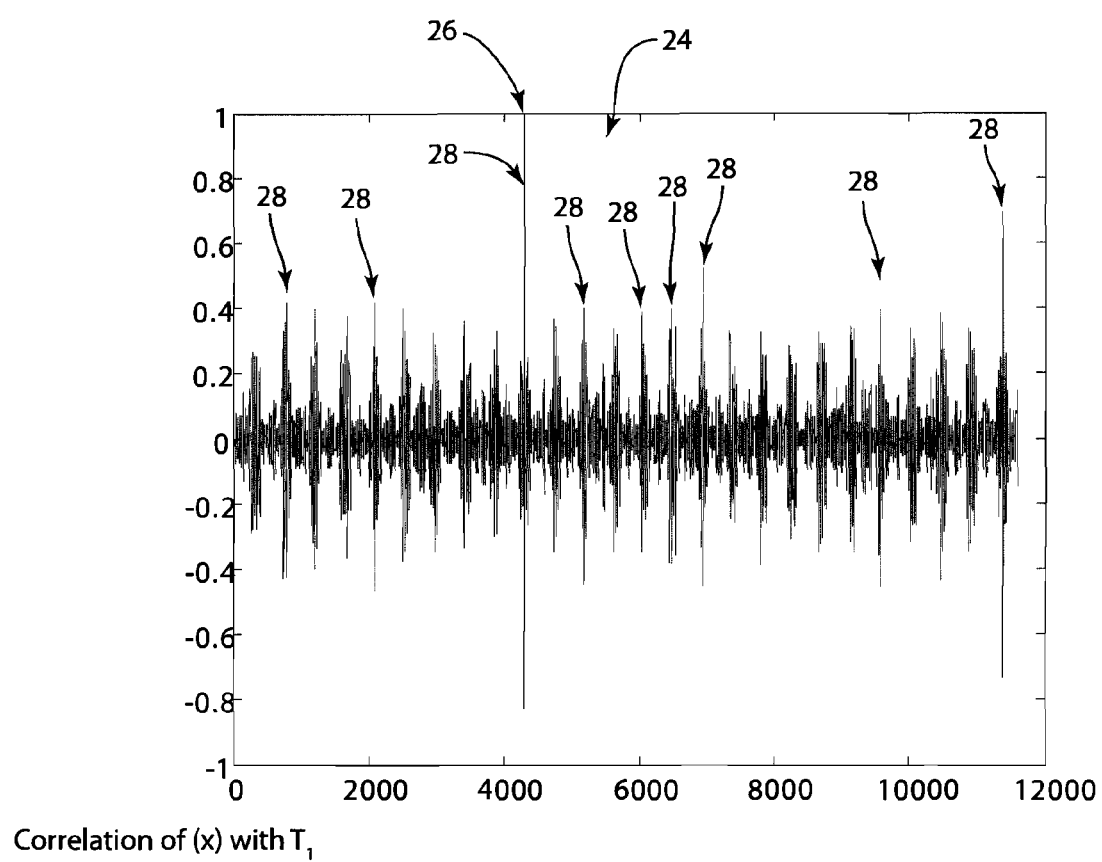
Figure 2C:
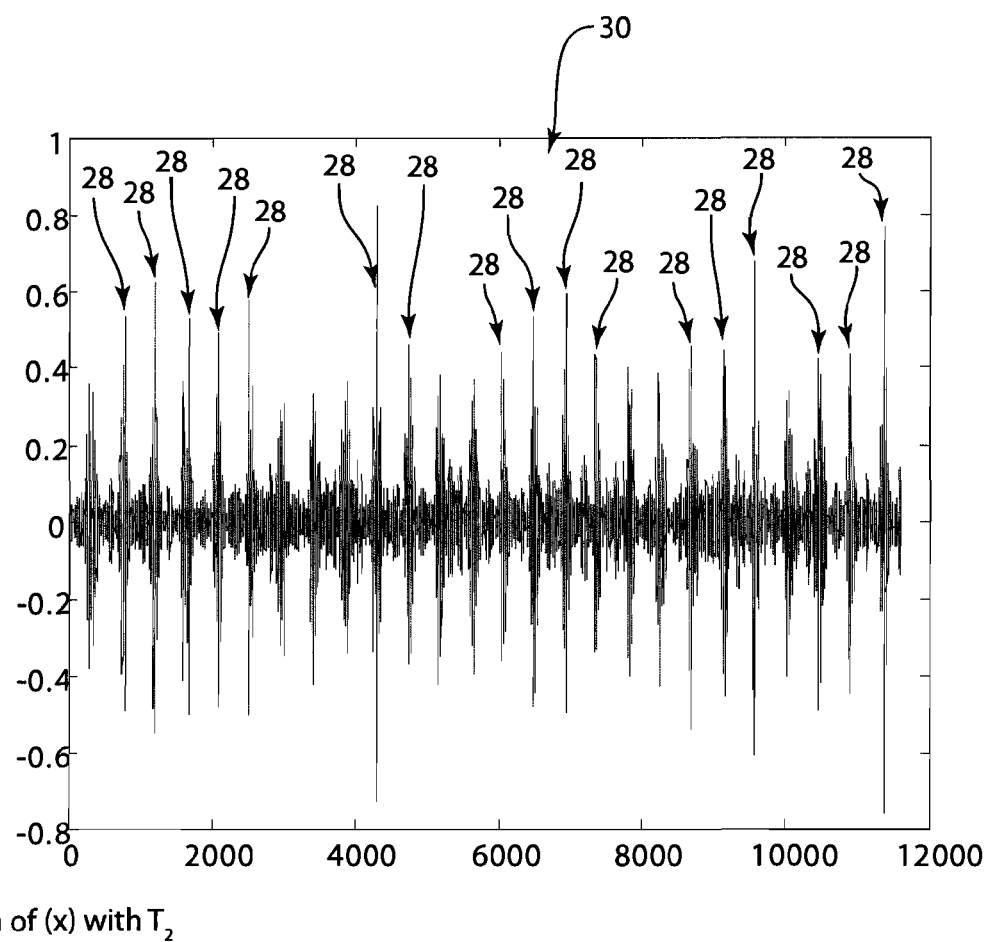
Figure 2D:
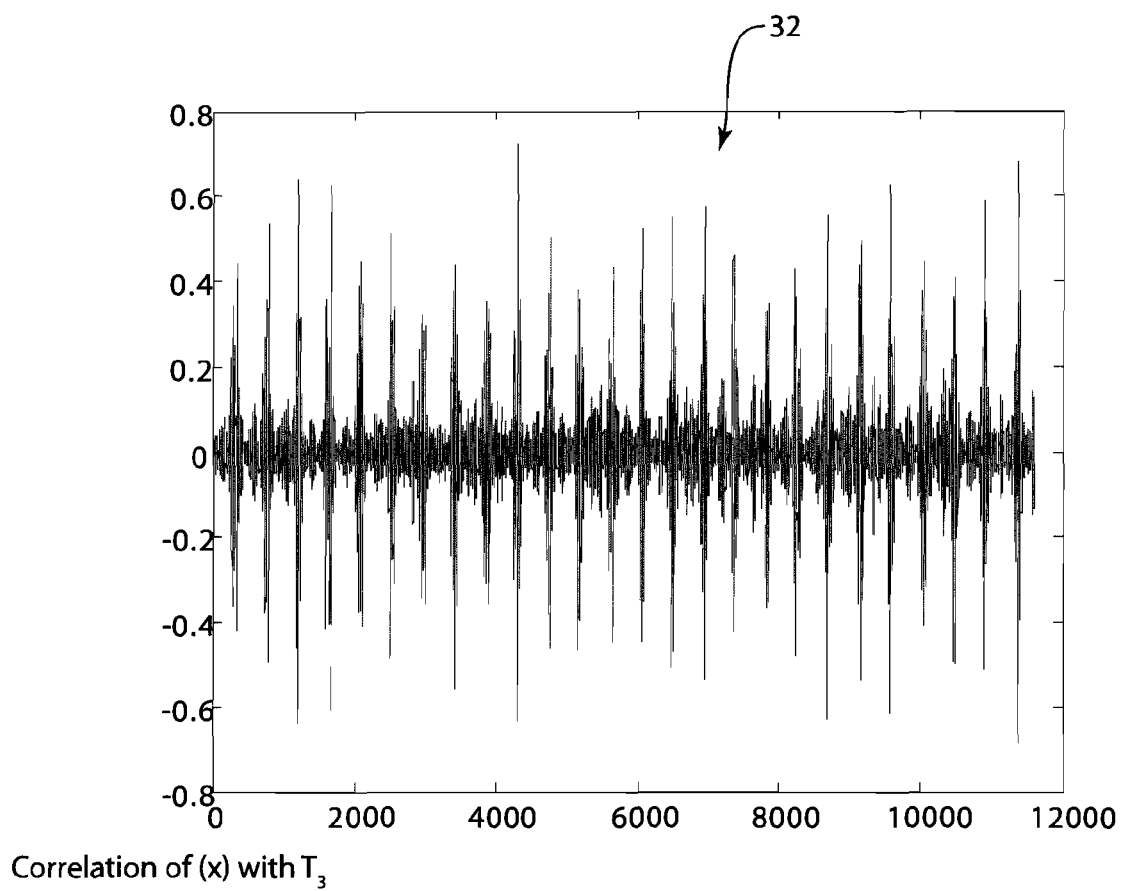
Figure 3:
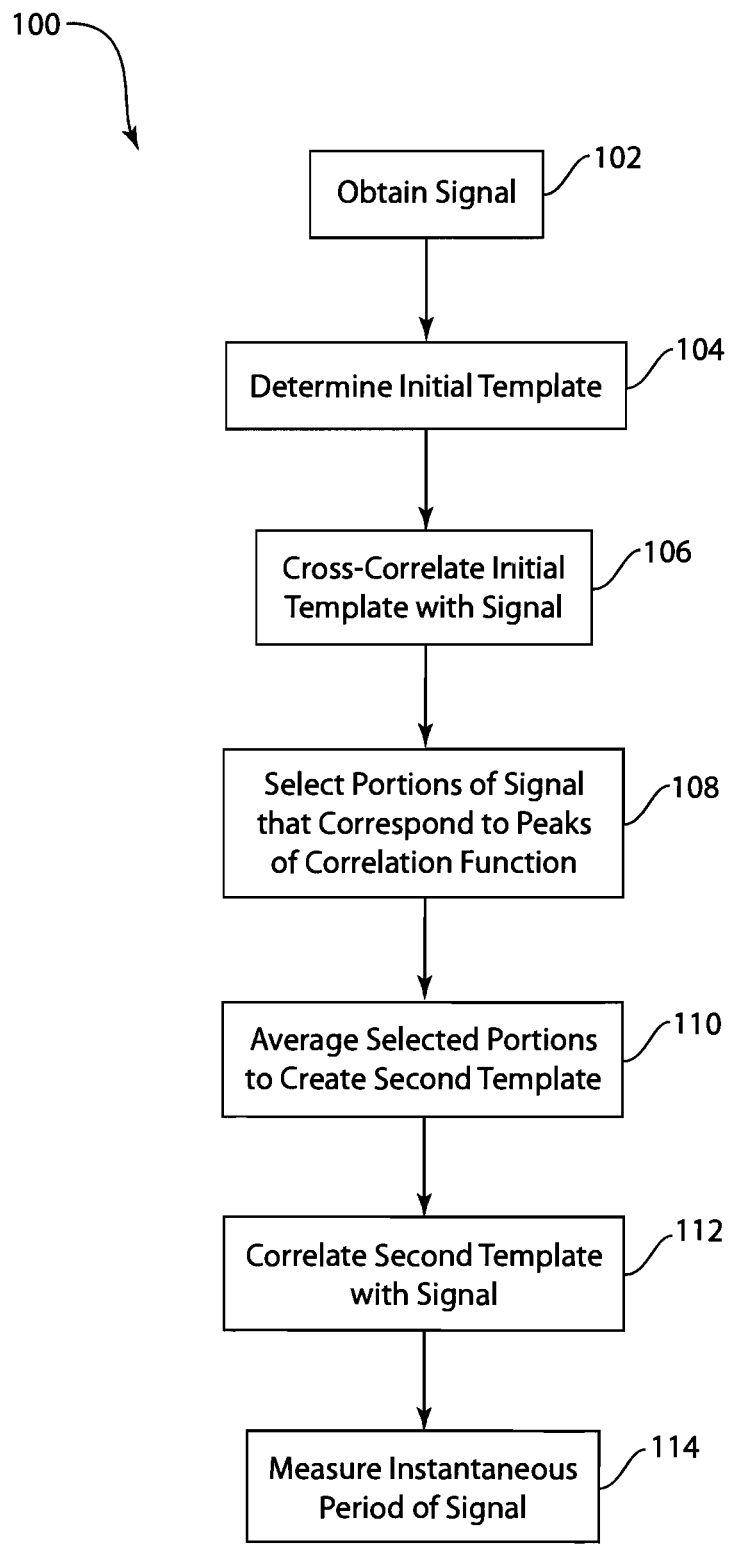
FIG. 3 is a flow chart depicting a general embodiment of the method for measuring the instantaneous period of a quasi-periodic signal.

FIG. 3 is a flow chart depicting the steps of an embodiment of a method for measuring the instantaneous period of a quasi-periodic signal, such as an ultrasound Doppler measurement of fetal heart rate. The steps depicted in FIG. 3 will be explained in greater detail herein with references to the graphs of FIGS. 1 and 2A-D.

First, a quasi-periodic signal, such as the Doppler shift of a returned ultrasound signal of fetal heart rate is obtained at step 102. This signal may be obtained through known ultrasound monitoring acquisition processes, or in the event of other applications, known methods or techniques used in acquiring the desired quasi-periodic signal. FIG. 2A is an exemplary graph depicting 27 beats of ultrasound Doppler signal including fetal heart signals mixed with unwanted noise. During the course of obtaining this signal, the signal may be filtered with a band pass filter to remove frequency components and noise artifacts that are not associated with the fetal heart beat.

Next, an initial template is determined at step 104. Referring to FIG. 1, the initial template 16 may be selected of a determined temporal size and temporal shift. In one embodiment, this initial template is the signal associated with a single fetal heart beat.

Next, the previously determined initial template 16 is cross correlated with the ultrasound signal 10 at step 106. In some embodiments, the ultrasound signal 10 may be divided into segments, such as the exemplarily depicted first segment 18, second segment 20, and third segment 22. The initial segment 16 may then be cross correlated with one of the ultrasound signal segments (18, 20, 22) to create a correlation signal. Cross correlation is a common technique used to measure the similarity of two signals or signal segments, in this case, the initial segment 16 and the ultrasound signal 10. FIG. 2B depicts a graph of the first correlation signal 24 between the ultrasound signal 10 of FIG. 2A and an initial template selected from the ultrasound signal between sample numbers 4300 and 4700. Therefore, the first correlation signal 24 exhibits a maximized correlation peak 26 at the segment selected as the initial template.

Referring back to FIG. 3, at step 108, portions of the ultrasound signal 10 that correspond to the peaks of the first correlation signal 24 are selected. To identify the peaks of the first correlation signal 24, a peak amplitude threshold may be established. By way of example, a peak amplitude threshold of 0.4 may be selected and any correlation peaks that meet or exceed this threshold are selected. With reference to FIG. 2B, there are nine selected peaks 28 of the first correlation signal 24 and the portions of the ultrasound signal 10 that correspond to these peaks are selected.

At step 110, the selected portions of the ultrasound signal 10 are averaged to create a second template. Then, at step 112, the second template is cross correlated with the ultrasound signal 10 to create a second correlation function. FIG. 2C depicts a graph of the second correlation signal 30. By viewing this graph, it is noticeable that the amplitude peaks of the second correlation signal 30 are higher and more defined on average than those of the first correlation signal 24.

The instantaneous period of the fetal heart rate may be measured at step 114 for each heart beat using the refined second correlation signal 30 and measuring the period between the correlation peaks.

In an alternative embodiment, the same 0.4 amplitude threshold or another determined threshold may be used to select correlation peaks from the second correlation signal 30 that meet or exceed the threshold. These selected peaks 28 of the second correlation signal 30 may be used to select the corresponding portions of the underlying ultrasound signal 10 such that these selected portions may be averaged to create a third template. The third template may in turn be cross correlated with the ultrasound signal 10 in order to produce a third correlation signal 32, which is depicted in FIG. 2D. Again, the amplitude of the correlation peaks of the third correlation signal 32 are on average higher and better defined than those of the second correlation signal 30. Thus, the third correlation signal 32 may alternatively be used to measure the beat-to-beat instantaneous period of the fetal heart.

Figure 4:
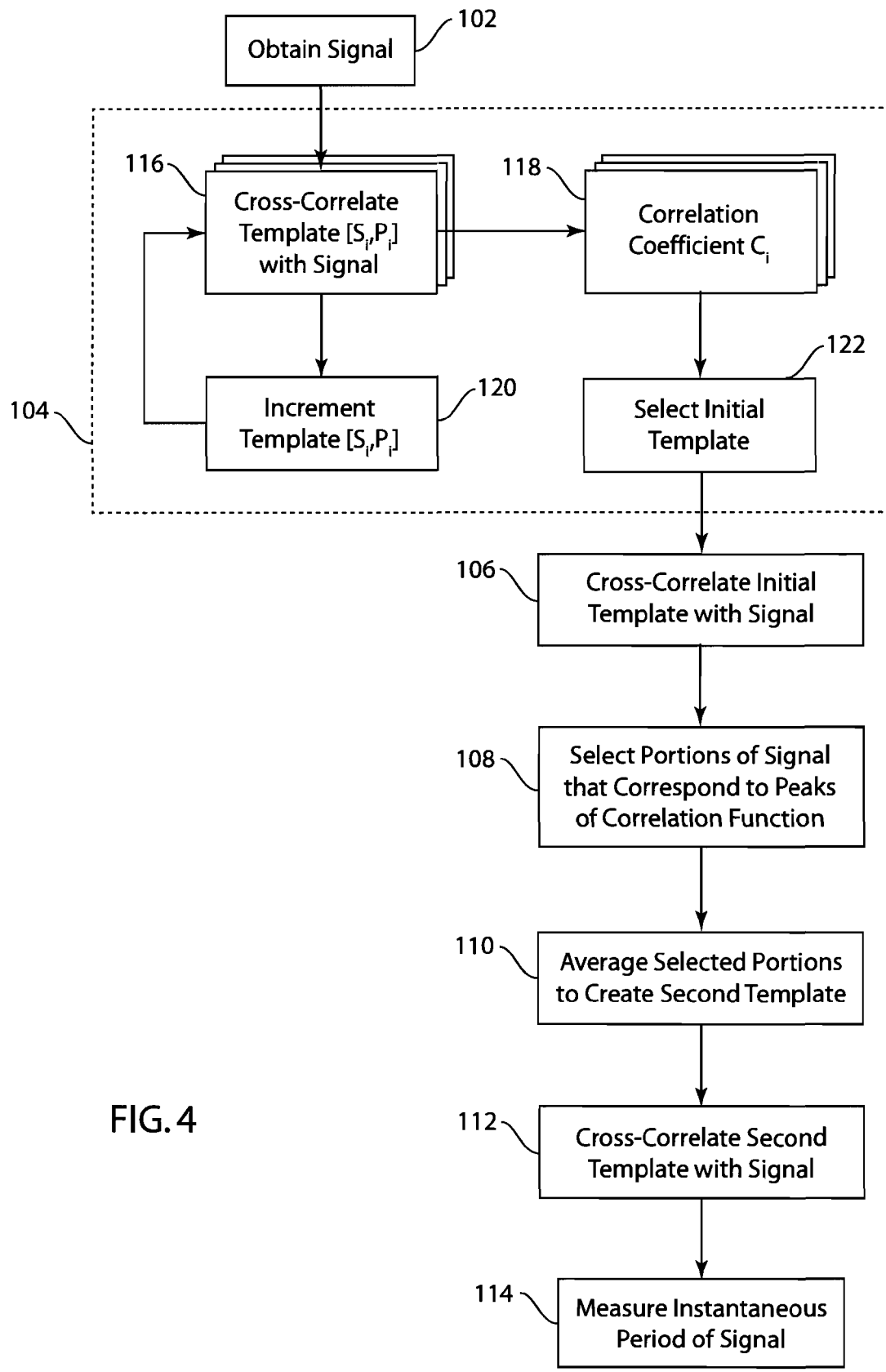
FIG. 4 is a more detailed flow chart of an embodiment of the method of FIG. 3.

FIG. 4 is a flow chart depicting a more detailed embodiment of the method depicted in the flow chart of FIG. 3. More specifically, the flow chart of FIG. 4 depicts a more detailed embodiment of the step of determining the initial template 104. As indicated in FIG. 1, the initial template is of a temporal size (S) and temporal shift (P). The initial template is determined by first selecting a template ($S_i$, $P_i$) from the ultrasound signal 10, or an ultrasound signal segment (i.e. first segment 18), and this template is cross correlated with the ultrasound signal 10 at step 116. This produces a correlation signal, and a corresponding correlation coefficient ($C_i$) is calculated at step 118. The correlation coefficient $C_i$ is a numeral value that represents the correlation between the template ($S_i$, $P_i$) and the signal 10. The correlation coefficient $C_i$ may be temporarily stored on a data storage medium that is internal or external to the system or device performing the disclosed method.

Next, at step 120, the template ($S_i$, $P_i$) is incremented in either the size of the template ($S_{i+1}$), the shift of the template ($P_{i+1}$), or both ($S_{i+1}$, $P_{i+1}$). These increments are denoted as reference number 34 in FIG. 1. Then, step 116 is repeated to cross correlate the new incremented template with the signal to obtain, at step 118, a new correlation coefficient ($C_{i+1}$). This correlation coefficient ($C_{i+1}$) is also temporarily stored on the data storage medium. These steps are repeated throughout a predetermined number of increments to the size and shift of the template in order to produce a plurality of correlation coefficients representing the correlation between each of the incremented templates and the signal. These correlation coefficients are all at least temporarily stored on the data storage medium. Then, at step 122, one of templates ($S_n$, $P_n$) is selected and stored to be the initial template. This selection of one template from all of the various templates created may be based upon the obtained corresponding correlation coefficients $C_n$ from step 118. The template ($S_n$, $P_n$) with the maximum correlation coefficient $C_n$ may be selected in step 122 as the initial template to be used in the rest of the steps of the method 100.

Figure 5:
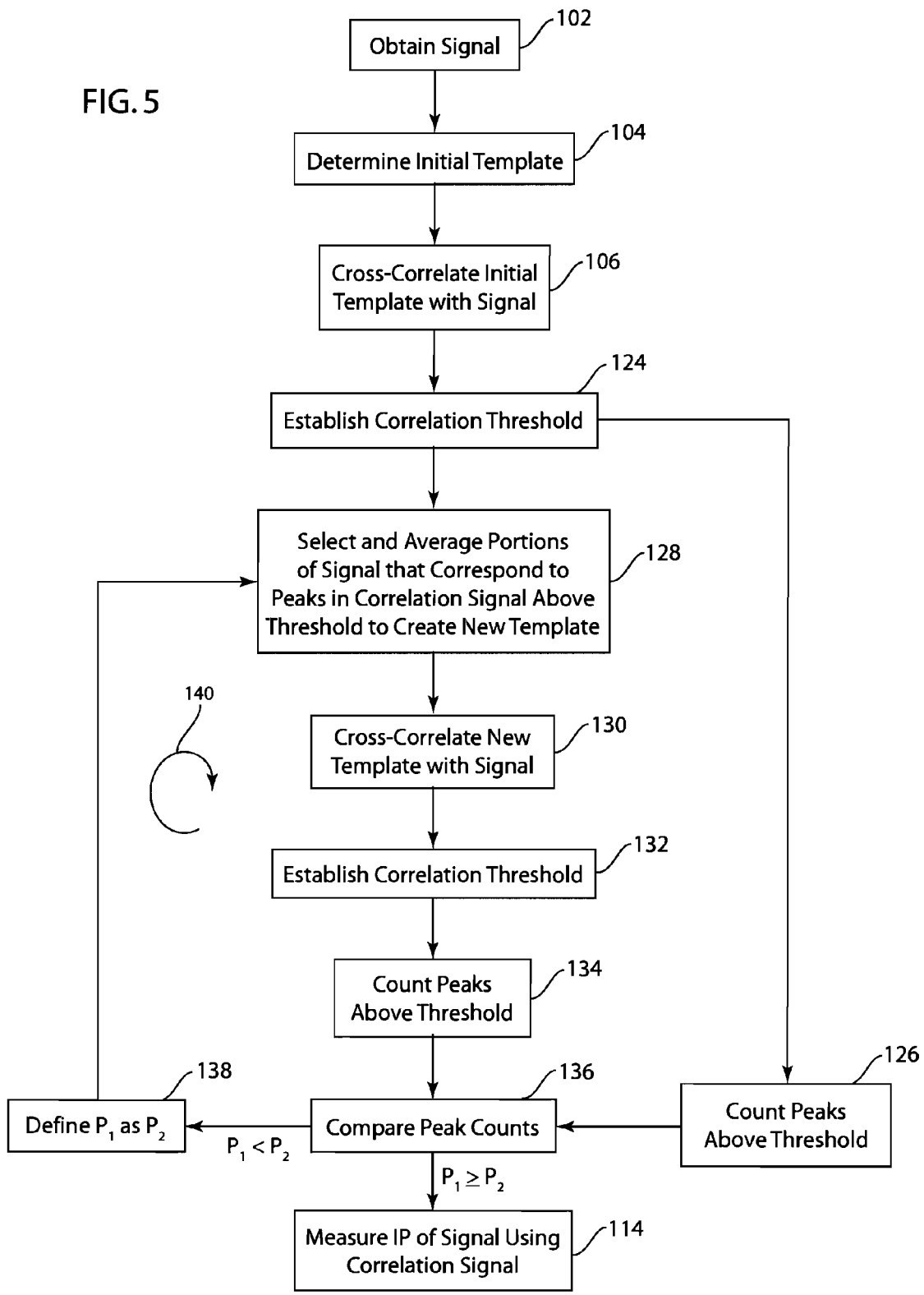
FIG. 5 is a flow chart that depicts the initial steps of an embodiment of the method for measuring the instantaneous period of a quasi-periodic signal.

FIG. 5 depicts a flow chart of a more detailed embodiment of the method 100 depicted in FIG. 3. The method depicted in the flow chart of FIG. 5 presents more detailed steps in the place of steps 108, 110, and 112 of the method 100 of FIG. 3.

In the method depicted in the flow chart of FIG. 5, after the initial template is cross correlated with the signal in step 106, a correlation threshold is established in step 124. At step 126, the correlation peaks above the threshold established in 124 are counted. The counted number of peaks is stored for later reference. In one embodiment, the counted number of peaks is stored as value $P_1$.

At step 128, the portions of the signal obtained in step 102 that correspond to the peaks in the correlation signal above the threshold established in step 124 are selected and averaged to create a new template. At step 130, the new template is cross correlated with the signal obtained in step 102.

Next, a correlation threshold is established at step 132 for the new correlation signal. The correlation threshold established in step 132 may be the same as the correlation threshold established in step 124 or may be adjusted according to another criteria or property of the signal such as would warrant the newly established correlation threshold in step 132 to be higher or lower than the one established in step 124. As an example, an elevated threshold in step 132 may be desirable to reflect the increased average amplitudes of the correlation peaks.

Then, at step 134, the peaks in the new correlation signal that exceed the correlation threshold established in step 132 are counted. The counted number of peaks in step 134 is stored for later reference. In one embodiment, the counted number of peaks is stored as the value $P_2$.

At step 136, the peak counts ($P_1$, $P_2$) from steps 126 and 134 are compared. If the peak count from step 126 is greater than or equal to the peak count ($P_2$) obtained in step 134, then the instantaneous period of the obtained signal is measured in step 114 using the new correlation signal. If, in step 136, the peak count ($P_1$) obtained in step 126 is less than the peak count ($P_2$) obtained in step 134, then peak count $P_1$ is redefined as the value of peak count $P_2$ at step 138 and the method is repeated with steps 128-136 through loop 140 with a newly created template using the peaks identified in step 134. The method of loop 140 may be repeated until at step 136, the peak count $P_1$ is greater than or equal to the peak count $P_2$, and the instantaneous period is measured in step 114.

Figure 6:
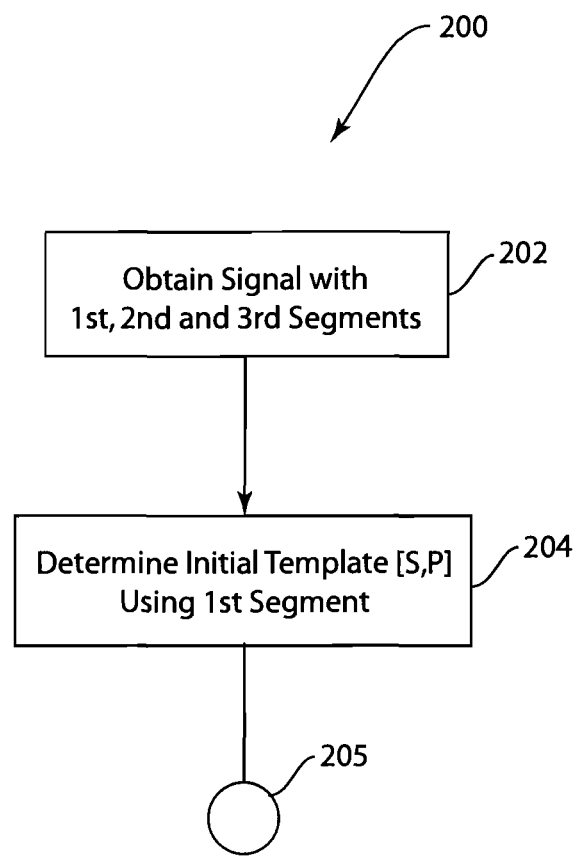
FIG. 6 depicts an alternative embodiment of a method for measuring the instantaneous period of a quasi-periodic signal.

FIG. 6 depicts the first two steps of an alternative embodiment of a method 200 of measuring the instantaneous period of a quasi-periodic signal. The method 200 includes the embodiments that will be disclosed herein with respect to the flow charts of FIGS. 7, 8, and 9. Referring back to FIG. 6, a signal with at least first, second, and third segments is obtained at step 202. The signal obtained in step 202 may be represented by the ultrasound signal 10 in FIG. 1 which has been divided into equally sized first segment 18, second segment 20, and third segment 22.

Back to the flow chart of FIG. 6, at step 204 an initial template with a size S and a shift P is determined using the first segment of the signal obtained in step 202. The method 200 of FIG. 6 terminates in node 205. Alternative embodiments of the method 200 are depicted in FIGS. 7, 8, 9a and 9b, continuing the method 200 from node 205.

The initial template is obtained in the manner previously described wherein the initial template may be a portion of the first signal segment of a predetermined time length or a previously stored model template. Alternatively, the initial template may be derived by cross correlating a plurality of incremented templates ($S_i$, $P_i$) to determine the incremented template with the greatest correlation coefficient with the first signal segment to use as the initial template.

Figure 7:
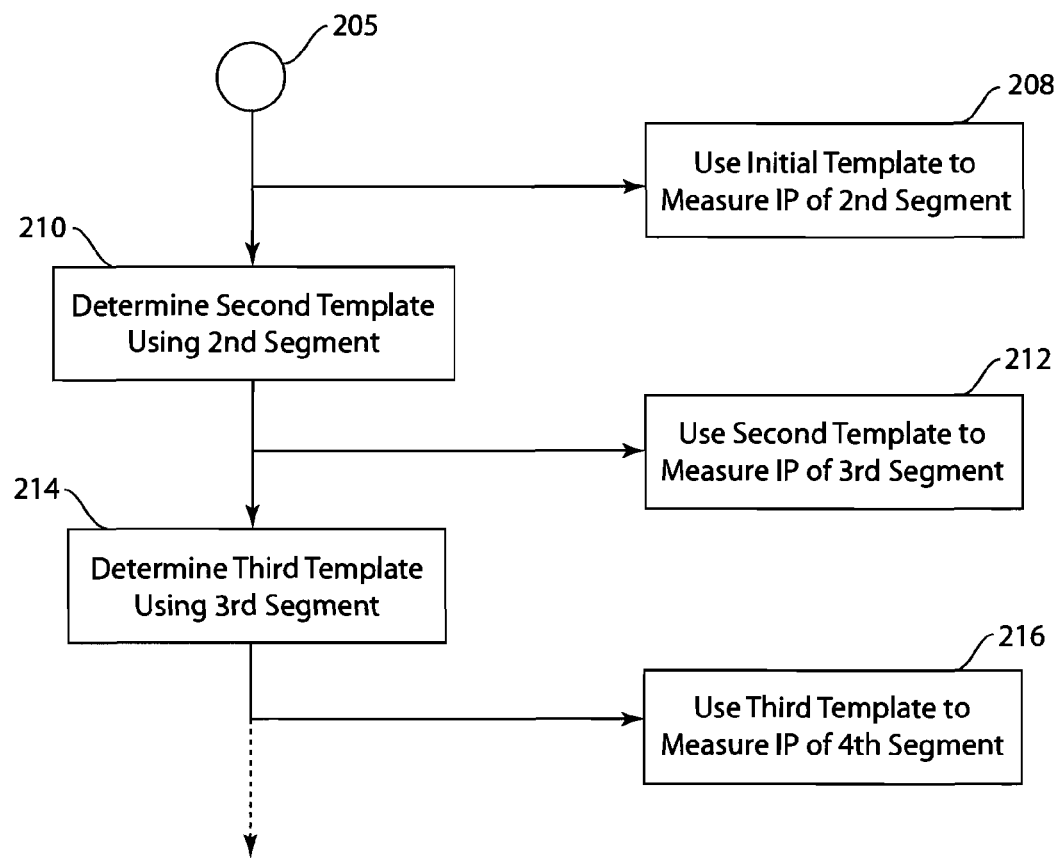
FIG. 7 is a flow chart depicting an embodiment of the steps continuing from the flow chart of FIG. 6.

Now referring to the embodiment of the method 200 depicted in the flow chart of FIG. 7, in step 208, the initial template from step 204 is used to measure the instantaneous period of the second segment. This is performed by cross correlating the initial template with the second signal segment to produce a second correlation signal from which the instantaneous period of the second signal segment may be obtained.

In step 210, a second initial template is determined using the second segment. The second initial template may be determined in the same manner as the initial template was; however, in this step, the second signal segment is used. Therefore, the second initial template may be derived by cross correlating a plurality of incremented templates ($S_i$, $P_i$) to determine the incremented template with the greatest correlation coefficient with the second signal segment to use as the second initial template.

Next, at step 212, the second initial template is used to measure the instantaneous period of the third signal segment. This is done by cross correlating the second initial template with the third signal segment to obtain a third correlation signal from which the instantaneous period is measured.

In some embodiments, the obtained signal may comprise more than a first, second, and third segment. In these embodiments, the method may continue in the following manner as will be described for a fourth segment for as many segments are in the obtained signal.

In step 214, a third initial template is determined using the third signal segment. The third template may be determined in the same manner as the initial template and second initial templates were determined. The third initial template is then used in step 216 to measure the instantaneous period of the fourth signal segment. This is done by cross correlating the third initial template with the fourth signal segment in order to obtain a fourth correlation signal. The instantaneous period of the fourth signal segment may be measured from the fourth correlation function.

Thus, the embodiment of the method disclosed in the flow chart of FIG. 7 may be used as a method for processing a continuously running quasi-periodic signal that may be divided into any number of segments and processed with an updated initial template by updating the initial template with each newly processed signal segment and applying the updated initial template to the newly collected segment of the obtained quasi-periodic signal.

Figure 8:
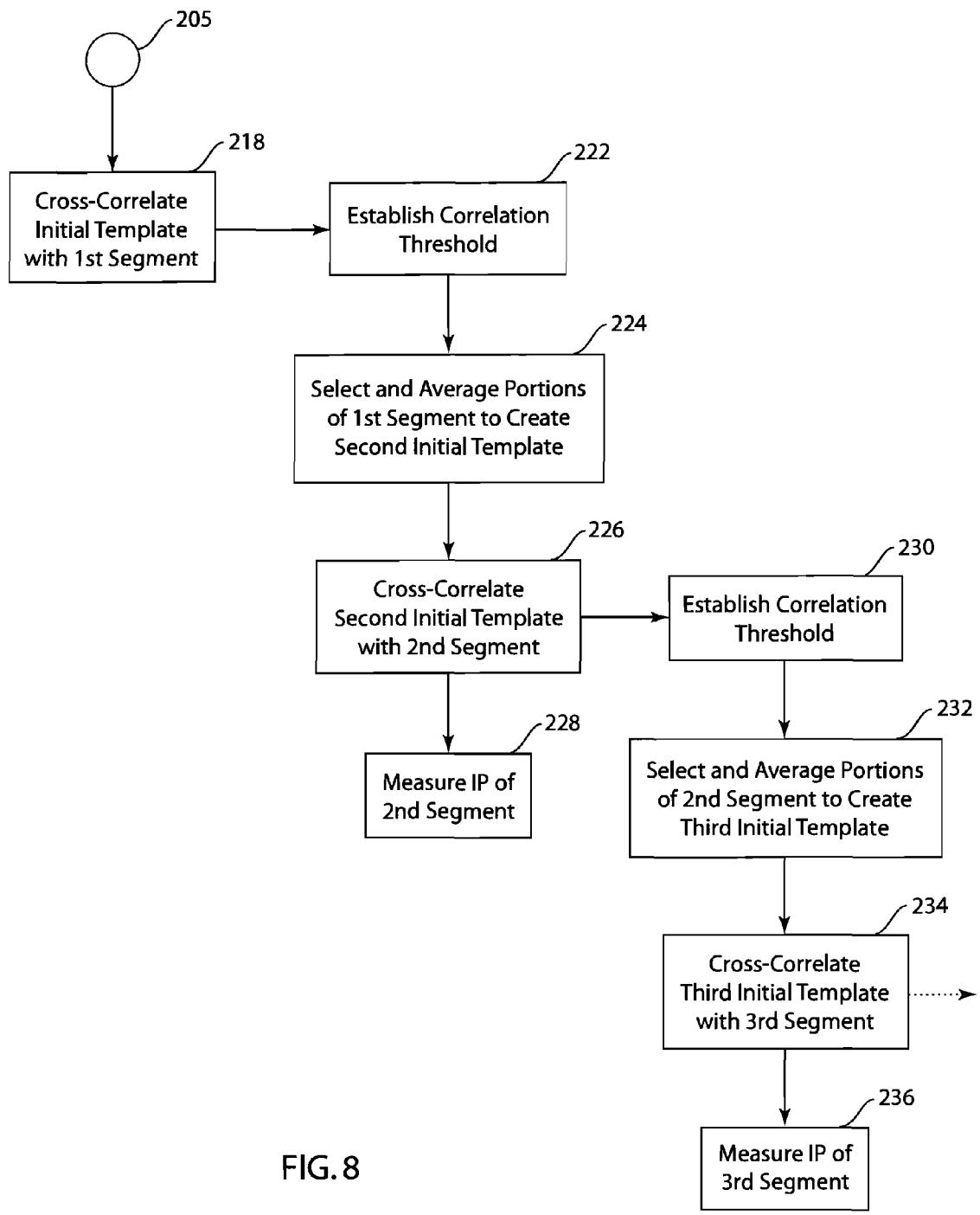
FIG. 8 is a flow chart depicting an embodiment of the steps continuing from the flow chart of FIG. 6.

FIG. 8 depicts a flow chart of an alternative embodiment of the method 200 starting in FIG. 6. In the embodiment depicted in the flow chart of FIG. 8, the initial template from step 204 is cross correlated with the first signal segment in step 218. This cross correlation produces a first correlation signal exhibiting a plurality of correlation peaks.

In step 222, a correlation threshold is established for use with the first correlation signal from the cross correlation of step 218. In step 224, the established correlation threshold is used to select portions of the first signal segment that correspond to the peaks in the first correlation signal that exceed the established threshold. The selected portions of the first signal segment are averaged to create a second initial template.

The second initial template is cross correlated in step 226 with the second signal segment to produce a second correlation signal exhibiting a plurality of correlation peaks. At step 228, the instantaneous period of the second signal segment is measured using the second correlation signal.

In step 230, a correlation threshold for the second correlation signal is established. In step 232, the correlation threshold is used with the second correlation signal to select the portions of the second signal segment that correspond to the peaks of the second correlation signal that exceed the correlation threshold. The selected portions of the second signal segment are averaged in step 232 to create a third initial template.

The third initial template is cross correlated with the third signal segment in step 234 to produce a third correlation signal. The third correlation signal includes a plurality of correlation peaks. The third correlation signal is used in step 236 to measure the instantaneous period of the third segment. The instantaneous period is measured by measuring the period between correlation peaks.

The above disclosed steps of the embodiment of the method 200 of the flow chart in FIG. 8 may be continuously repeated in the above-described fashion in order to process an obtained quasi-periodic signal with more than three segments. In the alternative, this embodiment of the method 200 may be used to process a continuously obtained quasi-periodic signal wherein the currently obtained segment of the signal is processed with an initial template created from the data of the previously obtained segment of the same signal. Thus, over the course of processing the continuously obtained signal, the template used to determine the instantaneous period of the signal is continuously updated to maintain accuracy in the instantaneous period determination.

Figure 9A:
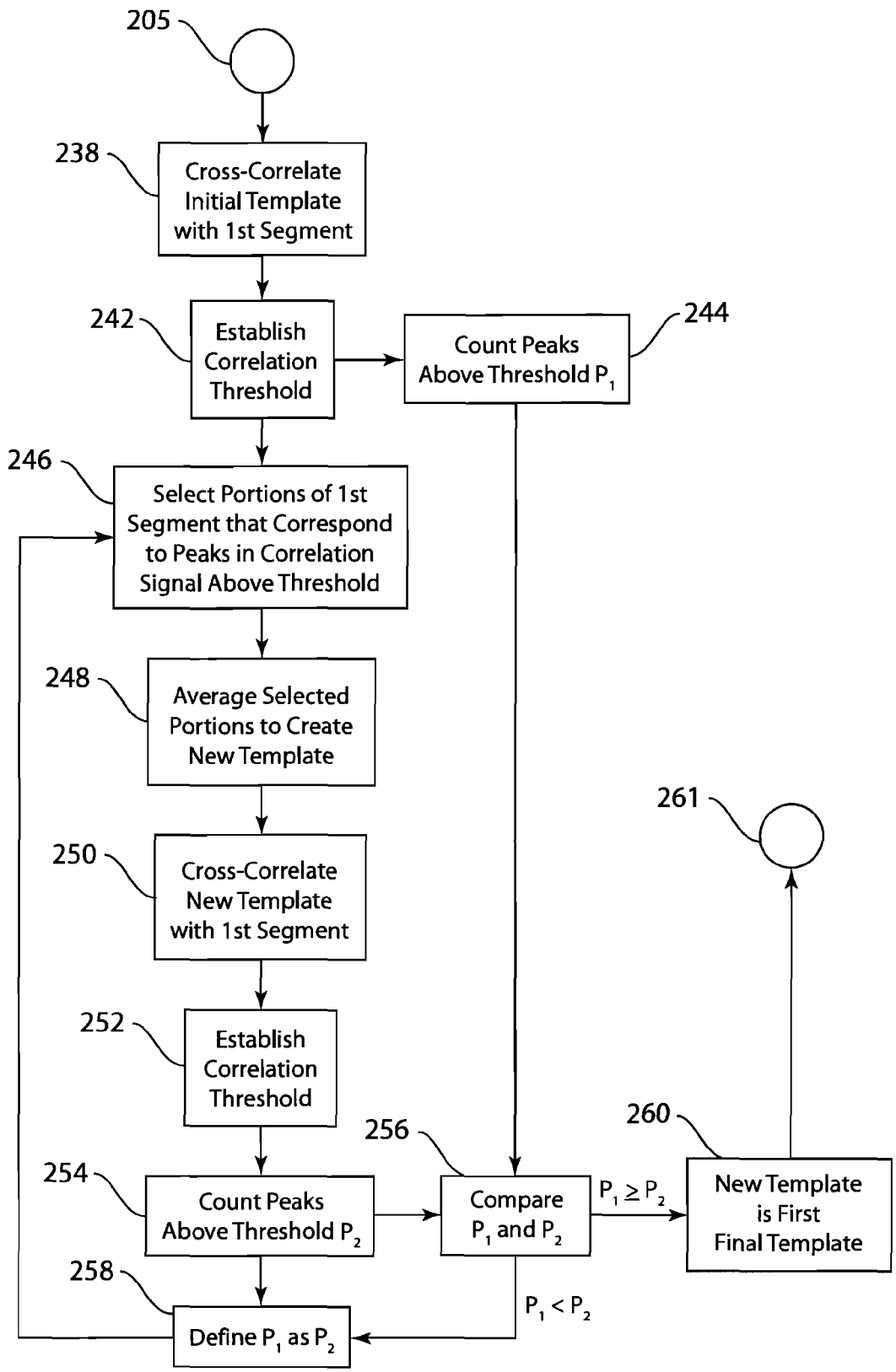
FIG. 9 is a flow chart depicting an alternative embodiment of the steps continuing from the flow chart of FIG. 6.
Figure 9B:
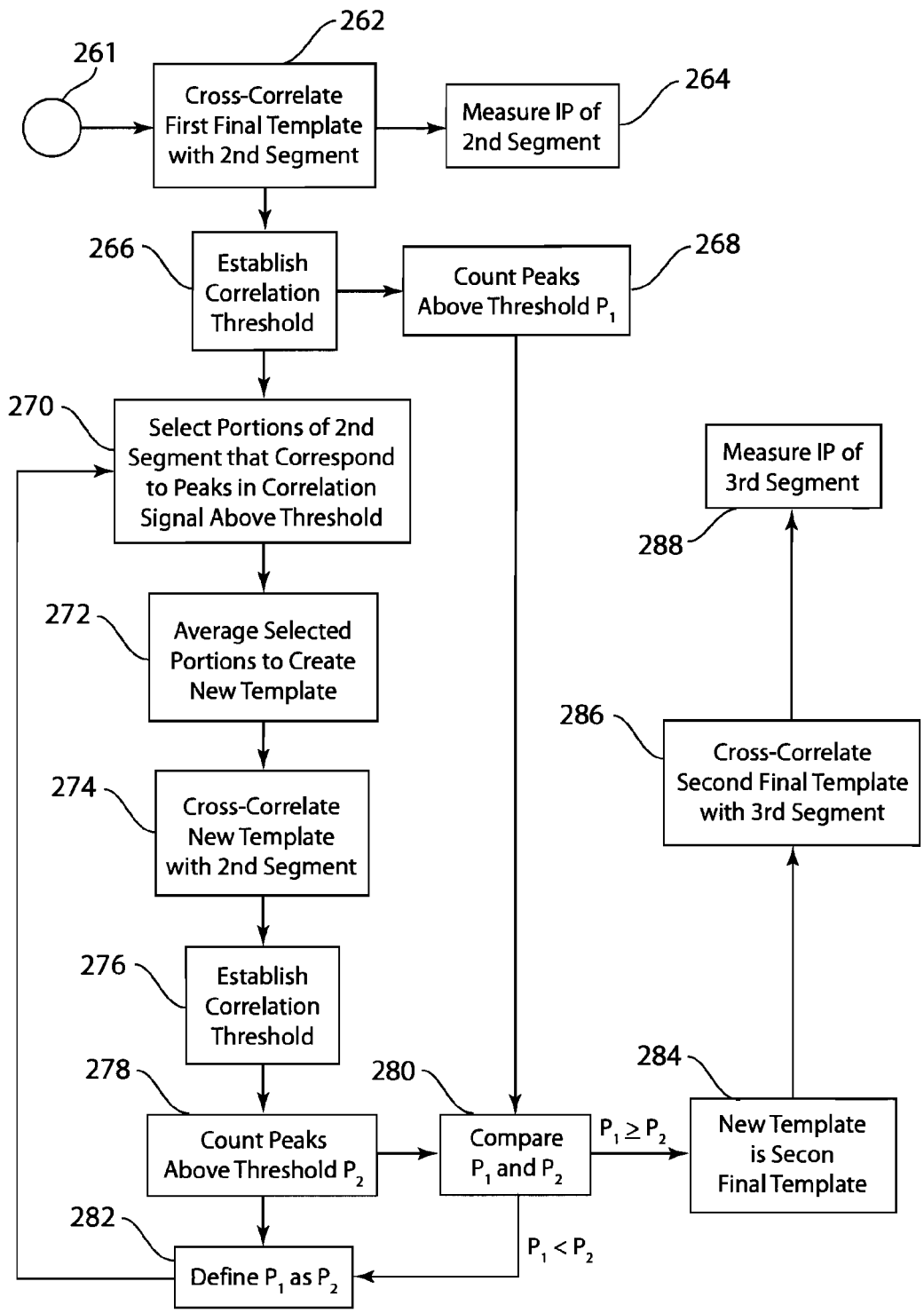

FIGS. 9a and 9b depict a flow chart of a still further embodiment of the method 200 continued from FIG. 6. In this embodiment, the template used to produce the correlation signal from which the instantaneous period is measured is maximized for each segment before it is applied to the next signal segment to measure the instantaneous period of the signal during that segment.

At step 238, the initial template is cross correlated with the first signal segment of the obtained signal, resulting in the first correlation signal. A correlation threshold is established in step 242 and the number of correlation peaks in the first correlation signal that exceed the established threshold are counted and this count is stored, for example, as value $P_1$ in step 244.

Next, portions of the first signal segment that correspond to the correlation peaks in the first correlation signal above the established threshold are selected in step 246. In step 248, these selected portions of the first signal segment are averaged to create a new template. In step 250, the new template is cross correlated with the first signal segment to obtain a new correlation signal. A correlation threshold for the new correlation signal is established in step 252 and in step 254 the correlation peaks that exceed the correlation threshold established in step 252 are counted. This count of the correlation peaks is stored, for example, as value $P_2$. It is to be understood that in some embodiments, the correlation threshold established in step 252 may be the same correlation threshold as is established in step 242; however, in other embodiments, a new correlation threshold may be established for each new correlation signal in order to more accurately control the counted number of correlation peaks.

In step 256, the count of the correlation peaks from step 244 represented as value $P_1$ and the count of the correlation peaks from step 254 represented by value $P_2$ are compared. If the count $P_1$ is less than the count $P_2$ then the value $P_1$ is redefined in step 258 as the current value of $P_2$ and steps 246 through 254 are repeated to obtain a new value for $P_2$ for comparison at step 256. If the value $P_1$ is greater than or equal to the value of $P_2$, then at step 260 the new template created in step 248 is stored as the first final template.

FIG. 9b continues from node 261 wherein the method of FIG. 9a left off. The first final template is then cross correlated in step 262 with the second signal segment to produce a second correlation signal. The second correlation signal is used in step 264 in order to measure the instantaneous period of the second signal segment. The instantaneous period may be measured by measuring the period between each correlation peak of the second correlation signal. Additionally, at step 266, a correlation threshold is established for the second correlation signal and at step 268 the correlation peaks above the correlation threshold are counted and may be stored as value $P_1$. The correlation threshold in step 266 is also used in step 270 wherein the portions of the second signal segment are selected that correspond to the correlation peaks in the second correlation signal that exceed the correlation threshold. In step 272, the selected portions of the second signal segment are averaged to create a new template.

In step 274, the new template is cross correlated with the second signal segment to produce a new correlation signal. Next, a correlation signal threshold is established in step 276 for the new correlation signal. In step 278, the correlation peaks in the new correlation signal that exceed the threshold established in step 268 are counted and may be stored as value $P_2$.

In step 280, the values of $P_1$ and $P_2$ are compared to each other. If the value $P_1$ is less than the value $P_2$, then in step 282 value $P_1$ is redefined as the current value of $P_2$ and steps 270 through 278 are repeated to establish a new value of $P_2$. Then again in step 280, the values of $P_1$ and $P_2$ are compared. The comparison in step 280 thus provides a loop whereby successive new templates and correlation signals are created for the second signal segment, with each new template being created using a greater number of segments of the second signal segment as the templates used become more accurate. The loop ends at step 280 when the correlation signal from the new template yields less than or equal the number of correlation peaks above the established threshold than the previous template did over the same second signal segment.

At this point, the current new template is defined to be the second final template at step 284. This is due to the fact that no more correlation peaks were identified with the new template, than with the previous template, which was evidenced by the value $P_1$ being equal to or greater than the value $P_2$. The second final template is then cross correlated with the third signal segment in step 286 to produce a third correlation signal. The third correlation signal is used in step 288 to measure the instantaneous period over the course of the third signal segment.

As with previously disclosed embodiments, the currently described embodiment may be likewise applied to signals obtained with more than three segments, or a continuously obtained signal that is incrementally divided into segments as it is obtained. In viewing the operation of the embodiment of the method 200 of FIG. 9, derivation of the first final template may require multiple cycles of steps 246 through 254; however, for the subsequent signal segments, relatively few cycles may be needed as only minor adjustments to the template may be required for each new signal segment.

In an alternative embodiment of the method 200 described with respect to FIGS. 9a and 9b, after or concurrent to step 252 of cross correlating the first final template with the second segment, the additional step of determining a new initial template (S,P) from the second segment (not depicted) is performed.

The new initial template may be determined as previously described above, starting with a template of a temporal size (S) and a temporal shift (P). The new initial template is determined by first selecting a template $(S_i, P_i)$ from the second segment, and this template is cross correlated with the second segment. This produces a correlation signal and a corresponding correlation coefficient $(C_i)$. Next, the template $(S_i, P_i)$ is incremented in either the size of the template $(S_{i+1})$, the shift of the template $(P_{i+1})$ or both $(S_{i+1}, P_{i+1})$. Then, the cross correlation is repeated using the new incremented template and the second segment to obtain a new correlation coefficient ($C_{i+1}$). These steps are repeated throughout a predetermined number of increments to the size and shift of the template in order to produce a plurality of correlation coefficients representing the correlation between each of the incremented templates and the signal.

One of the templates ($S_n$, $P_n$) is selected and stored to be the initial template. The selection of one template from all of the various templates created may be based upon the obtained corresponding correlation coefficients $C_n$. The template ($S_n$, $P_n$) with the maximum correlation coefficient $C_n$ may be selected as the initial template that is to be cross correlated with the second segment. The correlation signal from the cross correlation between the new initial template and the second segment is then used in steps 266 and 268 to identify the correlation peaks that are above the established correlation threshold.

In this disclosed alternative embodiment, a new final template is created using not only the iterave process of refining the template, but using a new initial template for each of the segments of the quasi-periodic signal to be analyzed.

In still further alternatives to the method embodiments disclosed with respect to FIGS. 6-9, after the initial template (S, P) has been determined using the first segment in step 204, an output may be produced that identifies the instantaneous period of the first segment. As a practical matter, this determination may often be delayed, in that in typical embodiments, the template produced from the previous segment is used to analyze the next segment of the quasi-periodic signal. Therefore, in some embodiments, no measurement of instantaneous period is obtained for the first signal segment as the initial template is used to measure the instantaneous period of the second segment. However, in other embodiments, other methods for determining instantaneous period may be used to provide an analysis or an estimation of the instantaneous period of the first signal segment. These analyses may include short term analysis (STA) or other forms of analysis whereby the first period of the first segment, or other peak detection techniques are used to determine, or estimate, the instantaneous period of the quasi-periodic signal over the first signal segment.

Figure 10:
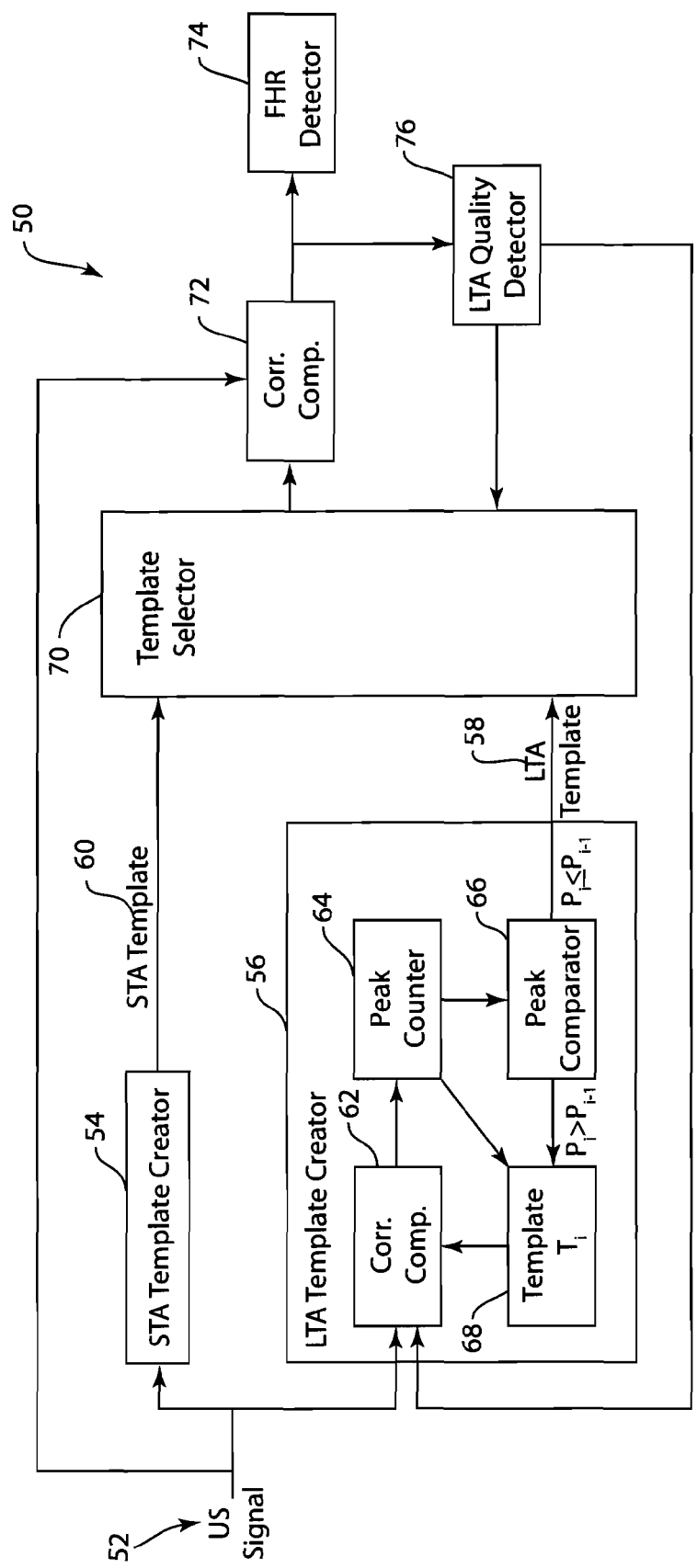
FIG. 10 is a system diagram of an embodiment of a system for measuring the instantaneous period of quasi-periodic signal.

FIG. 10 depicts an embodiment of a system 50 for measuring the instantaneous period of quasi-periodic signal. The system 50, which more specifically, is one embodiment for obtaining the instantaneous fetal heart rate from a returned ultrasound signal. The quasi-periodic returned ultrasound signal 52 is obtained from an ultrasound transducer through commonly known ultrasound techniques. The returned ultrasound signal is provided to a short term analysis (STA) template creator 54. The STA template creator creates a short term analysis template 60 for analysis of the ultrasound signal 52. The short term analysis template 60 may be a predefined model STA template or may be a selected portion of the returned ultrasound signal 52. If the STA template 60 is a selected portion of the returned ultrasound signal 52, then the selected portion is of a generally short duration, for example, on the order of 1-2 seconds of data.

The returned ultrasound signal 52 is also provided to a long term analysis (LTA) template creator 56. The LTA template creator operates according to one of the methods as disclosed herein to produce a long term analysis template 58. The LTA template creator 56 includes a correlation computer 62 that correlates a template $T_i$ with the ultrasound signal 52, or a segment thereof. A peak counter 64 either defines or uses a predetermined correlation threshold in order to identify and count the correlation peaks of the correlation signal received from the correlation computer 62. The peak counter 64 produces a count ($P_i$) of the peaks meeting or exceeding the correlation threshold.

A peak comparator 66 compares the number of peaks ($P_i$) counted by the peak counter 64 for the current correlation signal compared to the number of peaks ($P_{i-1}$) counted by the peak counter 64 for the previous correlation signal. If the number of peaks counted for the current correlation signal ($P_i$) exceeds the number of peaks counted for the previous correlation signal ($P_{i-1}$), then a template creator 68 averages the portions of the ultrasound signal that correspond to the peaks in the correlation signal detected by the peak counter 64 to create a new template $T_i$. The new template from template creator 68 is then applied to the same segment of the ultrasound signal by the correlation computer 62.

This process is repeated until the peak counter 64 identifies a number of peaks less than or equal to the number of peaks identified in the previous correlation signal. When the peak comparator 66 identifies that this condition is met, the current template $T_i$ is the LTA template 58 which is provided to the template selector 70. The template selector 70 receives both the LTA template 58 and the STA template 60. The template selector 70 selects one of the STA template 60 or the LTA template 58 to provide to the correlation computer 72. The correlation computer 72 also receives the ultrasound signal 52 and cross correlates the template selected by the template selector 70 with the ultrasound signal 52 to produce a correlation signal. This correlation signal is used by an FHR detector 74 to determine the instantaneous fetal heart rate in the ultrasound signal 52.

The correlation signal from the correlation computer 72 is also provided to an LTA quality detector 76. The LTA quality detector 76 determines the quality of the instantaneous fetal heart rate detection capability of the correlation signal produced by the correlation of the current LTA template 58 with the ultrasound signal 52. The LTA quality detector 76 may operate in a number of ways such as may be used to evaluate the quality of a signal obtained through signal processing. One exemplary embodiment of a methodology for the LTA quality detector 76 is that the LTA quality detector 76 constantly performs a correlation between the STA template 60 and the ultrasound signal 52.

Alternatively, the LTA quality detector 76 may receive the results of the cross correlation between the STA template 60 and the ultrasound signal 52 from another source. The LTA quality detector 76 may then compare the correlation signal from the STA template 60 versus the correlation signal from the LTA template 58. If the STA template 60 produces a correlation signal with the greater amplitude of correlation peaks, then the LTA quality detector 76 may indicate that the LTA template quality is low. If, on the other hand, the cross correlation of the LTA template 58 and the ultrasound signal 52 produces a correlation signal with the maximum amplitude correlation peaks compared to the correlation signal from the STA template 60, then the LTA quality detector 76 may indicate that the LTA template quality is high.

In a still further embodiment, the LTA quality detector 76 may calculate the signal to noise ratio (SNR) for the correlation signal produced using the LTA template 58. The calculated SNR may be compared to a predetermined scale for acceptable LTA correlation signals to determine LTA quality. Alternatively, the LTA quality detector 76 may also calculate the SNR for the correlation signal from the STA template 60 and compare the calculated LTA and STA SNR values to determine LTA template quality.

The LTA quality detector 76 provides the high/low LTA quality determination to both the template selector 70 as well as the correlation computer 62 of the LTA template creator 56. The template selector 70 operates such that when the template selector 70 receives an indication of a high quality LTA template, the template selector 70 selects the LTA template 58 to provide to the correlation computer 72. If the template selector 70 receives an indication of a low quality LTA template, then the template selector 70 selects the STA template 60 to provide to the correlation computer 72.

The LTA template creator 56 operates in conjunction with the template selector 70 such that when the LTA template creator 56 receives an indication that the LTA template quality is low, then the LTA template creator 56, and more specifically the correlation computer 62 of the LTA template creator 56, begins the process of creating a new LTA template 58 to replace the current LTA template which has been deemed to be producing a low quality result. Similarly, once the LTA quality detector 76 has indicated that the current LTA template 58 is resulting in a high quality correlation signal, then the LTA template creator 56 stops its calculation of a new LTA template.

The system as disclosed in FIG. 10 provides the signal processing advantage of optimizing the instantaneous fetal heart rate detection between short term analysis and long term analysis methods. The short term analysis method has the advantage of being constantly available to analyze the ultrasound signal as it uses a predefined STA template. As disclosed herein, the LTA method of instantaneous fetal heart rate detection produces an improved quality of result; however, experiences a lag time as the LTA template must be created from collected ultrasound signal data. Also, the LTA analysis method has the further challenge of resulting in a correlation signal of a varying quality. This requires the need to periodically update the LTA template to maintain a high quality correlation signal.

Thus, the system 50 provides a solution to these problems by providing the STA template for a base level of instantaneous fetal heart rate detection while the LTA template is unavailable for instantaneous fetal heart rate detection. However, once the LTA template becomes available for a high quality instantaneous FHR detection, the system 50 switches over to the LTA method of analysis to produce a higher quality of instantaneous FHR detection.

Some of the embodiments of the system and method as disclosed herein may be performed and/or implemented through solely the use of a computer. In these embodiments, the components or steps may be performed by a series of dedicated use computers, by computer programs or computer program modules as specifically designed for use on a general purpose computer to carry out the steps and functions as disclosed herein. In these computer implemented embodiments, the technical effect of the presently disclosed system and method is to provide a more accurate analysis of quasi-periodic signals.

As noted previously, the present description has focused on specifically the quasi-periodic signal of the Doppler shift of an ultrasound signal due to a fetal heart beat. It should be likewise be understood that the system and method as disclosed herein may likewise be also used in other types of biosignal monitoring applications, such as EEG, or even in non-biological applications, such as measuring the angular velocity of a piece of rotating machinery.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of measuring the instantaneous period of a quasi-periodic signal, the method comprising:
    obtaining a quasi-periodic signal;
    determining an initial template of a determined size and shift with a computer by:
    performing a cross-correlation between the quasi-periodic signal and a template segment of the quasi-periodic signal, the template segment being of a pre-determined size and a pre-determined shift, to obtain a selection coefficient;
    incrementing the pre-determined size and the pre-determined shift of the template segment to create an incremented template segment;
    repeating the cross-correlation between the quasi-periodic signal and the incremented template segment through a plurality of increments to obtain selection coefficients for each of a plurality of incremented template segments; and
    selecting the incremented template with a maximum selection coefficient;
    performing a cross-correlation between the initial template and the quasi-periodic signal to obtain an initial correlation signal;
    establishing a first correlation threshold;
    selecting portions of the quasi-periodic signal that correspond to peaks of the initial correlation signal greater than the first correlation threshold;
    counting a number of peaks in the initial correlation signal greater than the first correlation threshold;
    averaging the selected portions to create a second template;
    performing a cross-correlation between the second template and the quasi-periodic signal to obtain a second correlation signal;
    establishing a second correlation threshold; and
    counting the number of peaks in the second correlation signal greater than the second correlation threshold;
    wherein if the number of peaks counted in the initial correlation signal is greater than or equal to the number of peaks counted in the second correlation signal, measuring the instantaneous period between the peaks in the second correlation signal and
    wherein if the number of peaks counted in the initial correlation signal is less than the number of peaks counted in the second correlation signal:
    selecting the portions of the quasi-periodic signal that correspond to the peaks of the second correlation signal that are greater than the second correlation threshold;
    averaging the selected portions of the quasi-periodic signal to create a third template; and
    performing a cross-correlation between the third template and the quasi-periodic signal to obtain a third correlation signal.

2. The method of claim 1 wherein the quasi-periodic signal comprises a first segment and a second segment and the step of determining an initial template is performed using the first segment of the quasi-periodic signal.

3. The method of claim 2 wherein the steps of performing a cross-correlation between the initial template and the quasi-periodic signal and performing a cross-correlation between the second template and the quasi-periodic signal are performed using the second segment of the quasi-periodic signal, and measuring the instantaneous period of the second segment.

4. The method of claim 1, wherein the quasi-periodic signal comprises a first segment, a second segment, and a third segment and the step of determining an initial template is performed using the first segment.

5. The method of claim 4 further comprising:
measuring the instantaneous period in the second segment by determining the initial template using the first segment, cross correlating the initial template with the second segment and using the cross-correlation between the initial template and the second segment to obtain a correlation signal of the second segment; and
measuring the instantaneous period in the third segment by determining a second initial template from the second segment, cross correlating the second initial template with the third segment, and using the cross-correlation between the second initial template and the third segment to obtain a correlation signal of the third segment.

6. The method of claim 4, further comprising:
performing a cross-correlation between the initial template and the first segment to obtain an initial correlation signal;
establishing a first correlation threshold;
selecting portions of the first segment that correspond to peaks of the initial correlation signal greater than the first correlation threshold;
averaging the selected portions to create a second template;
measuring the instantaneous period of the second segment using the second template;
performing a cross-correlation between the initial template and the second segment to obtain a second correlation signal;
establishing a second correlation threshold;
selecting portions of the second segment that correspond to peaks of the second correlation signal greater than the second correlation threshold;
averaging the selected portions to create a third template; and
measuring the instantaneous period of the third segment using the third template.

7. The method of claim 4 further comprising:
cross-correlating the initial template with the first segment to create an initial correlation signal of the first segment;
determining a first final template by:
counting the number of peaks in a previous correlation signal, wherein the previous correlation signal is initially the initial correlation signal of the first segment; and
counting a number of peaks in a current correlation signal, wherein the current correlation signal is initially the second correlation signal of the first segment;
wherein if the number of peaks counted in the previous correlation signal is greater than or equal to the number of peaks counted in the current correlation signal:
establishing the current template as the first final template; and
measuring the instantaneous period, between the peaks in the second correlation signal;
wherein if the number of peaks counted in the previous correlation signal is less than the number of peaks counted in the current correlation signal:
selecting the portions of the first segment that correspond to the peaks of the current correlation signal;
averaging the selected portions of the first segment to create a current template; and
cross-correlating the current template with the first segment to determine a new current correlation signal of the first segment;
repeating the above steps until the number of peaks counted in the current correlation signal is greater than or equal to the number of peaks counted in the previous correlation signal;
cross-correlating the first final template with the second segment to create an initial correlation signal of the second segment; and
measuring the instantaneous period in the second segment using the initial correlation signal of the second segment.

8. The method of claim 7 further comprising:
determining a second final template by:
counting the number of peaks in a previous correlation signal, wherein the previous correlation signal is initially the initial correlation signal of the second segment; and
counting a number of peaks in a current correlation signal, wherein the current correlation signal is initially the second correlation signal of the second segment;
wherein if the number of peaks counted in the previous correlation signal is greater than or equal to the number of peaks counted in the current correlation signal:
establishing the current template as the second final template; and
measuring the instantaneous period between the peaks in the current correlation signal;
wherein if the number of peaks counted in the previous correlation signal is less than the number of peaks counted in the current correlation signal:
selecting the portions of the second segment that correspond to the peaks of the current correlation signal;
averaging the selected portions of the first segment to create a current template; and
cross-correlating the current template with the second segment to determine a new current correlation signal of the second segment;
repeating the above steps until the number of peaks counted in the current correlation signal is greater than or equal to the number of peaks counted in the previous correlation signal;
cross-correlating the second final template with the third segment to create an initial correlation signal of the third segment; and
measuring the instantaneous period in the third segment using the initial correlation signal of the third segment.

9. A method of measuring an instantaneous period of a quasi-periodic signal, the method comprising:
obtaining a quasi-periodic signal;
determining an initial template of a determined size and shift with a computer by:
performing a cross-correlation between the quasi-periodic signal and a template segment of the quasi-periodic signal to obtain a selection coefficient, the template segment being of a pre-determined size and a pre-determined shift; and
incrementing the pre-determined size and a pre-determined shift of the template segment to create an incremented template segment;
repeating the cross-correlation between the quasi-periodic signal and the incremented template segment through a plurality of increments to obtain selection coefficients for each of a plurality of incremented template segments; and selecting the incremented template with a maximum selection coefficient as the initial template;
performing a cross-correlation between an initial template and the quasi-periodic signal to obtain an initial correlation signal;
counting peaks of the initial correlation signal greater than a first correlation threshold;
selecting portions of the quasi-periodic signal that correspond to the peaks of the initial correlation signal greater than the first correlation threshold;
averaging the selected portions of the quasi-periodic signal to create a second template;
performing a cross-correlation between the second template and the quasi-periodic signal to obtain a second correlation signal; and
counting peaks of the second correlation signal greater than the correlation threshold;
wherein if the second correlation signal has more counted peaks than the initial correlation signal, using the second template as the initial template and iteratively repeating the method until the initial correlation signal has a same number or more counted peaks than the second correlation signal; and
wherein if the initial correlation signal has the same number or more counted peaks than the second correlation signal, measuring the instantaneous period from the first correlation signal.

10. The method of claim 9, wherein the quasi-periodic signal is an ultrasound signal and the instantaneous period is a fetal heart rate.

* * * * *